United States Patent [19]

Humphreys

[11] Patent Number: 4,896,042

[45] Date of Patent: * Jan. 23, 1990

[54] DUAL MODE GERMICIDAL APPARATUS

[75] Inventor: Wesley G. Humphreys, Huntingdon Valley, Pa.

[73] Assignee: Dora DiCamillo 1988 Trust, Newtown, Pa.

[ * ] Notice: The portion of the term of this patent subsequent to Nov. 22, 2005 has been disclaimed.

[21] Appl. No.: 240,608

[22] Filed: Sep. 6, 1988

[51] Int. Cl.⁴ .............................................. A61L 2/10
[52] U.S. Cl. .................................. 250/435; 250/504 R; 250/504 H; 250/492.1; 250/455.1; 422/24
[58] Field of Search ............... 250/435, 504 A, 504 H, 250/492.1, 455.1; 422/24

[56] References Cited

U.S. PATENT DOCUMENTS 3,662,175 5/1972 Davidson et al. ................... 250/504
4,786,812 11/1988 Humphreys ....................... 250/455.1

Primary Examiner—Jack I. Berman
Attorney, Agent, or Firm—Ferrill and Logan

[57] ABSTRACT

A dual mode germicidal lamp is disclosed having a base section with a fan and filters and a germicidal lamp section with a handle and switch means which can be moved by hand over surfaces to be sterilized and plugged into the base section to allow air to be drawn across the lamps and sterilized.

11 Claims, 3 Drawing Sheets

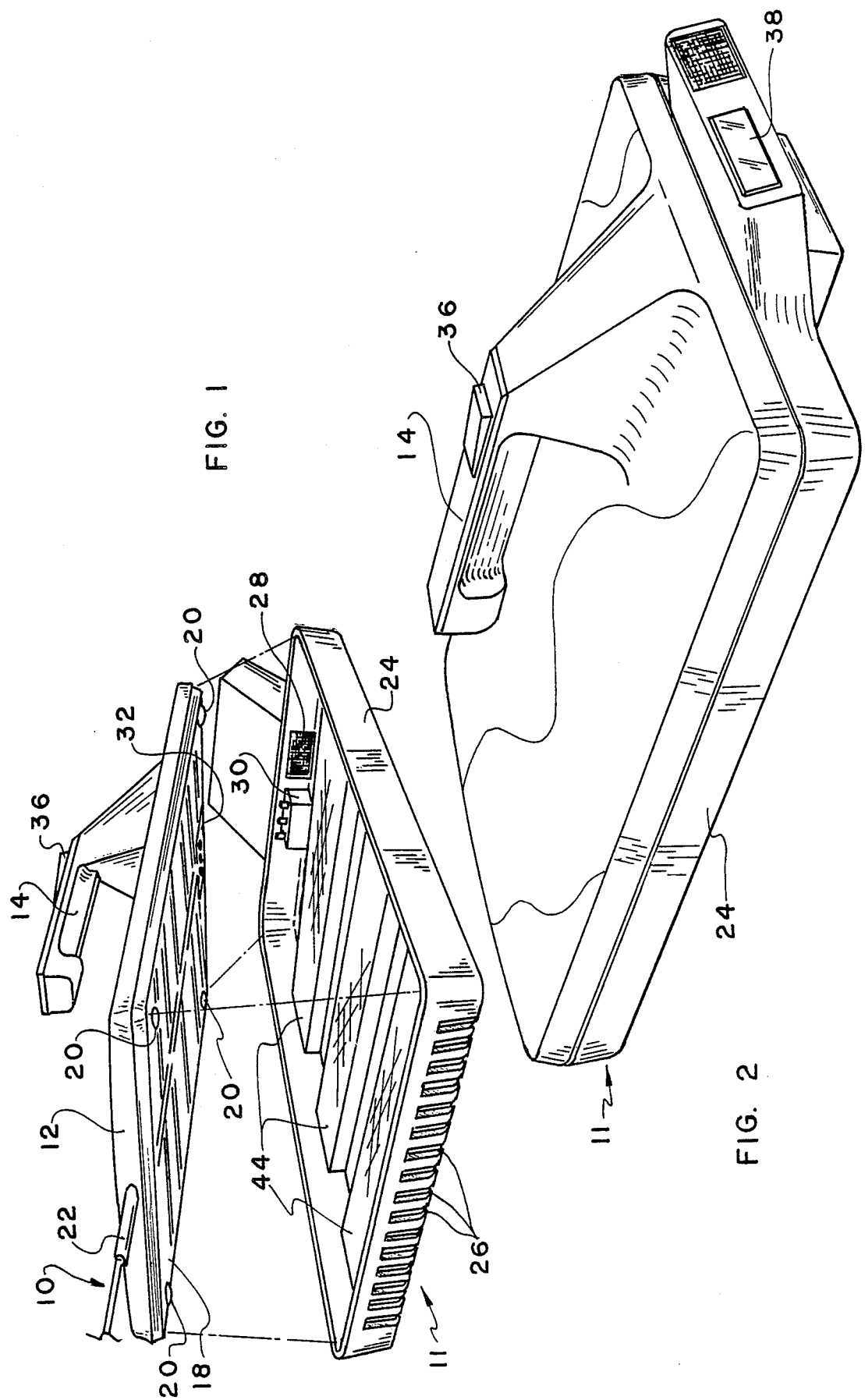

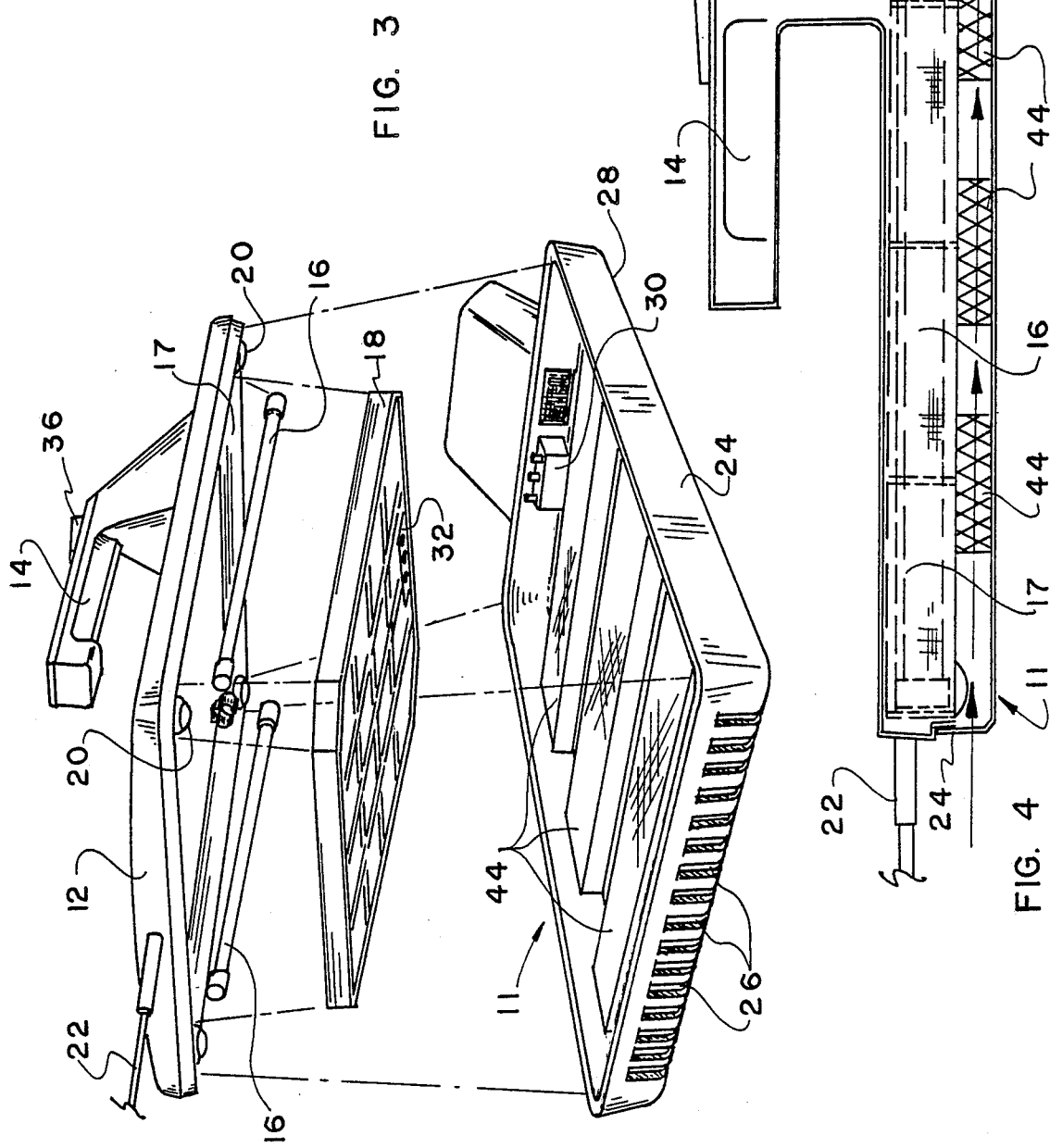

DUAL MODE GERMICIDAL APPARATUS

FIELD OF THE INVENTION

The present invention generally relates to an apparatus for killing germs and bacteria present in air or on various types of surfaces and which is capable of improved hand-held mobility. More particularly, a detachable base section is provided which, when disengaged, substantially reduces the weight of the apparatus during sterilization of exposed surfaces.

BACKGROUND OF THE INVENTION

It is often desirable to provide a sterile environment by killing any germs or bacteria which may be airborne or present on exposed surfaces. For example, parents may wish to sterilize their baby's bedroom so as to reduce the risk of their baby possibly being exposed to any germs or bacteria and consequently catching a cold. One germicidal lamp which performs such a function is disclosed in my copending U.S. patent application Ser. No. 935,794, now U.S. Pat. No. 4,786,812, dated Nov. 22, 1988, the disclosure of which is incorporated herein by reference. It comprises a single housing containing a plurality of ultraviolet light bulbs, together with a fan unit. The bulbs and fan operate simultaneously, with the fan causing germs or bacteria to be drawn into the housing, via air currents, where they are then killed by the light waves emitted by the ultraviolet bulbs. When a room is to be sterilized, the lamp, including both the bulbs and fan unit, is first swept over various exposed surfaces. Once those surfaces have been sterilized, the lamp is then left in a stationary position in a region of the room so that the air may also be sterilized. This germicidal lamp has been found to be effective in killing any germs or bacteria which are drawn into the lamp and come in contact with the light waves emitted by the bulbs.

One disadvantage associated with using such a germicidal lamp is that because both the bulbs and fan are contained within the same housing, their combined weights make the lamp somewhat unmanageable and unwieldy, when used in a hand-held sweeping mode.

Another disadvantage, directly related to the above mentioned one, is that in order to accommodate the weight of both the bulbs and fan, the housing must be made of a very sturdy, and consequently costly, material.

Finally, due to the design of the lamp and placement of the bulbs therein, sterilization of the air drawn through the unit is less than ideal. Both the intensity and time of exposure to the ultraviolet light waves are not at a maximum, and this somewhat detracts from the effectiveness with which germs or bacteria may be killed.

It is an object of the present invention to provide a more lightweight and portable germicidal lamp with improved hand-held mobility, when used to sterilize exposed surfaces.

Another object of the invention is to provide a germicidal lamp having a structure which will enable the ultraviolet light to come in closer and longer contact with air being drawn through the unit and targeted for sterilization.

Another object of the invention is to provide a lamp capable of sterilizing air and/or exposed surfaces in two separate modes.

Another object of the invention is to provide a germicidal lamp which, because of its design, is less costly to manufacture and therefore more affordable for home or office use.

SUMMARY OF THE INVENTION

The present invention is directed to the improved hand-held mobility of a germicidal lamp by use of a detachable base unit which, when detached, substantially decreases the weight of the lamp and, when in place on its base, increases the time of exposure of the air to be sterilized to the ultraviolet light.

The germicidal lamp of the invention is comprised of a housing structure made from a lightweight material having side walls, a top wall and an open lower end. A plurality of ultraviolet light bulbs are interposed within the housing which emit ultraviolet light waves. A grid is inserted within the housing spanning, lengthwise and widthwise, the open lower end of the housing to protect the bulbs from being damaged. Support means are affixed at the lower end of the side walls to support the housing and provide easy mobility over exposed surfaces. A reflector is carried by, and spans opposite side walls of, the housing to direct and intensify the light waves in a downward direction, toward the open end of the housing. A detachable base section having a lower wall and upwardly projecting side, front and rear walls which, when engaged with the lamp, provides a means for killing any germs or bacteria which may be airborne. Openings are included in the front and rear walls of the base to allow air to be drawn through the base section below the grid. A fan which draws air is carried by the rear wall of the base so that any bacteria carried by the air is exposed to the bulbs. In one embodiment, plug means are provided for a disconnectable electrical connection between the housing and the base. Also, electrical circuitry is provided on both the housing and the base to control operation of the bulbs, alone or in combination with the fan. Preferably, the electrical circuitry includes a first spring-biased and pressure-actuated switch, normally in an open position and located in the handle, which controls the bulbs. Also, a second switch is provided on the base to control operation of both the bulbs and fan when the housing is engaged with the base.

BRIEF DESCRIPTION OF THE DRAWINGS

The foregoing summary, as well as the following detailed description will be better understood when read in conjunction with the appended drawings. For the purpose of illustrating the invention, there is shown in the drawings an embodiment which is presently preferred, it being understood, however, that this invention is not limited to the precise arrangement and instrumentalities shown.

FIG. 1 is a top perspective view of the preferred embodiment of a dual mode germicidal lamp according to the present invention with the housing mounted on the base section.

FIG. 2 is an elevation view of the dual mode germicidal lamp of FIG. 1 with the housing disengaged from the base section FIG. 3 is a perspective view of the dual mode germicidal lamp of FIG. 2 with an exploded view of the housing.

FIG. 4 is a side elevation view of the dual mode germicidal lamp of FIG. 1 showing the air flow through the base.

DESCRIPTION OF A PREFERRED EMBODIMENT

Figure 5:
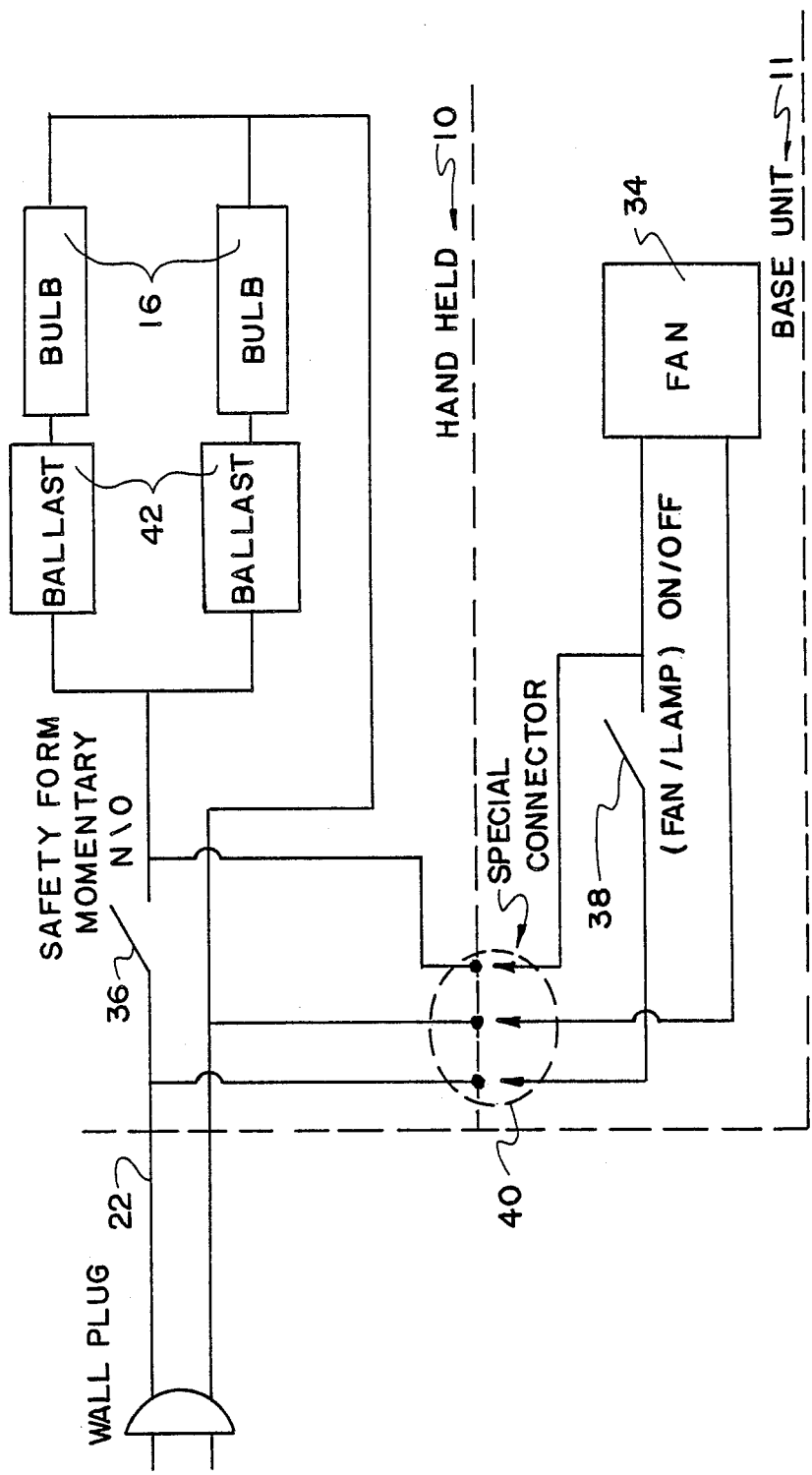
FIG. 5 shows an electrical block diagram of the dual mode germicidal lamp of the present invention.

Referring to the drawings, in detail, where like numerals indicate like elements throughout, there is shown in FIG. 2 a view of a dual mode germicidal lamp 10 in accordance with the invention. In this embodiment, the lamp unit 10 is shown disengaged from the base 11 and may be employed to sterilize exposed surfaces.

The lamp unit 10 of the present invention comprises a housing 12 (best seen in FIG. 3) having a handle 14 extending outwardly from the housing 12. A reflecting surface 17 is affixed to a top wall within the housing 12, for the purpose of directing and intensifying any light waves emitted within the housing 12 in a downward direction. A plurality of ultraviolet germicidal light bulbs 16 are interposed within the housing 14, below the reflecting surface 17, which emit ultraviolet light waves having a wavelength of approximately 253.7 nanometers.

In the present embodiment, a grid 18 is inserted within the housing 12 below the light bulbs 16 to protect the bulbs 16 from being damaged when the lamp unit 10 is disengaged from the base unit 11 and swept over various exposed surfaces. However, it should be understood that any other suitable type of protective means can be employed.

The light bulbs 16 of the lamp unit 10 are activated by depressing a spring-loaded switch 36 located in the handle 14 (best seen in FIG. 1), which is normally biased to an open position. The bulbs 16 are deactivated upon release of the switch 36. This feature of the invention protects against the possibility of a child turning on the lamp 10 and shining the bulbs 16 at his or her eyes, which may, in turn, cause injury. Because the switch 36 must be continuously depressed in order to activate the bulbs, the risk of such an event occurring is greatly reduced.

The housing 12 preferably includes support means to assist in sweeping the lamp unit 10 over flat surfaces. In the present embodiment, there are four ball-type rollers 20 affixed to and partially recessed within the corners of the housing 12 to permit the lamp unit to easily glide across a surface. However, it should be understood that any other suitable number or type of sweeping means can be employed.

The dual mode germicidal lamp of the present invention further includes a base unit 11 having a tray structure 24 as shown in FIGS. 2 and 3. The tray 24 includes a flat base and generally vertical side, front and rear walls adapted to engage and support the lamp unit 10, and also maintain the lamp unit spaced from the base of the tray. A plurality of apertures 26 are provided at one end of the tray 24 together with an exit opening 28 located at an end opposite from the apertures 26. The apertures 26 and exit opening 28 provide a means for allowing air to flow into and out of the tray 24 when the housing 12 is mounted onto the base 11. A fan unit 34 is affixed to the end of the tray 24 adjacent to the exit opening 28. The fan 34, when activated, causes air to be drawn from the outside of the base unit 11, and through the tray 24, immediately beneath the ultraviolet light bulbs 16. Any germs or bacteria which are caught in those air currents pass through the tray 24 and are subsequently exposed to the light waves emitted by the bulbs 16.

The base unit 11 preferably includes filtering means for both filtering and controlling the flow of air through the base unit 11, to maintain the exposure of the air to the light rays as long as possible. In the present embodiment a plurality of filters 44 (best seen in FIG. 3), made of a porous material, are affixed to the inside of the tray 24 to perform such a function. However, it should be understood that any suitable type of filtering means can be employed.

In the preferred embodiment, electrical connection means comprising a plug unit 30 attached to the tray 24 and a socket 32 carried by the housing 12 are included to provide a disconnectable electrical connection between the lamp unit 10 and the base 11. This combination is used when sterilizing the air within a room. A standard on-off switch 38 (best seen in FIG. 1) located adjacent to the fan 34 is used to activate both the bulbs 16 and fan 34 when the housing 12 and base 11 are used in combination.

In a preferred embodiment, the housing 12 and tray 24 are integrally molded from a lightweight and inexpensive plastic material.

The germicidal lamp 10 of the present invention may be used either by itself to sterilize exposed surfaces or in combination with the base unit 11 to sterilize the air inside a room. The operation of the lamp 10 by itself, and in combination with the base 11, will now be explained with reference to the schematic electrical block diagram in FIG. 5. When sterilizing exposed surfaces, the lamp 10 is disengaged from the base 11. Line voltage flows from a power source (not shown) through the plug cord 22 to a spring-biased switch 36, which is normally in an open position. When the switch 36 is depressed and the circuit is closed, line voltage passes through the ballasts 42 and activates the bulbs 16. The ballasts 42 convert the line voltage to 24 volts and 1.7 amps by means well known in the industry. The lamp 10 is then swept over exposed surfaces so that any germs or bacteria exposed to the light waves emitted by the bulbs 16 are killed.

To sterilize the air in a room, the lamp unit 10 is mounted onto the base 11. There is an electrical connection between the fan unit 34 and the lamp 10 at special connector 40. Standard on-off switch 38 activates both the fan 34 and the bulbs 16 of the lamp 10. The fan 34 causes air currents to be drawn into the base 11 and pass under the bulbs 16. Any germs or bacteria present in those air currents will be killed as they pass through the base 11 and are exposed to the light waves emitted by the bulbs 16. The sterilized air then flows out of the base 11 and back into the room.

Since the lamp unit 10 is not used in combination with the base 11 and fan 34 when sterilizing surfaces, the lamp 10 is therefore much more lightweight and manageable as compared to the prior art.

It will be recognized by those skilled in the art that changes may be made to the above-described embodiment of the invention without departing from the broad inventive concepts thereof. It is understood, therefore, that this invention is not limited to the particular embodiment disclosed, but it is intended to cover all modifications which are within the scope and spirit of the invention as defined by the appended claims.

What is claimed is:

1. In a lightweight portable ultraviolet germicidal lamp for killing both airborne and surface carried bacteria comprising a housing structure having side walls, a top wall and an open lower end; a grid spanning, lengthwise and widthwise, the open lower end of said housing; support means at the lower end of said side walls to support the housing and permit easy movement thereof over a surface with the grid closely adjacent to said surface; a reflector closely spaced from and facing said grid, said reflector carried by said housing and spanning between opposite side walls thereof; a plurality of ultraviolet germicidal lamps intermediate said reflector and grid extending lengthwise of said housing and parallel to said lengthwise grid; and handle means on said housing to permit the same to be readily moved by a user; the improvement comprising,

- a detachable base section having a lower wall and upwardly projecting front, rear and side walls to removably engage said housing structure and support the same with said grid spaced from the lower wall of said base section;
- openings in said front and rear walls to allow air to be drawn into a space between said grid and said lower wall; and
- a fan carried by said rear wall to draw air through the space between said grid and said lower wall whereby any bacteria carried by the air is exposed to said ultraviolet lamps.

2. An apparatus according to claim 1 including plug means providing a disconnectable electrical connection between said housing and said base.

3. An apparatus according to claim 1 further including electrical circuitry located in said housing and said base to control operation of said lamps and said fan.

4. An apparatus according to claim 3 wherein said electrical circuitry includes a first normally closed switch on said handle to control operation of said lamps when said housing is removed from said base and a second switch on said base to control operation of said lamps and said fan when said housing is engaged within said base.

5. An apparatus according to claim 4 wherein said first switch is spring-biased and movable to a closed position by manually depressing said switch to complete a circuit to said lamps.

6. An apparatus according to claim 2 wherein said plug means includes a socket connected to said first switch of said housing into which may be inserted a plug unit connected to said second switch of said base when said housing is engaged within said base.

7. An apparatus according to claim 1 wherein said support means includes a plurality of ball-type rollers partially recessed within said housing.

8. An apparatus according to claim 1 including filter means interposed between said side walls and adjacent to said lower wall of said base to prevent foreign particles from passing through said base and control movement of the air beneath the ultraviolet lamps.

9. An apparatus according to claim 8 wherein said filtering means includes a plurality of filters made of a porous material extending widthwise of said base.

10. An apparatus according to claim 1 wherein said lamps are in the form of elongated tubes extending substantially the full length of said apparatus and spaced uniformly widthwise of said housing.

11. A lightweight portable ultraviolet germicidal lamp for killing surface carried bacteria by being manually moved over a surface, said lamp comprising a housing structure having side walls, a top wall and an open lower end;

- a grid spanning, lengthwise and widthwise, the open lower end of the housing;
- support means at the lower end of the side walls to support the housing and permit easy movement thereof over a surface with the grid closely adjacent to the surface;
- a reflector closely spaced from and facing said grid, said reflector carried by said housing and spanning between opposite side walls thereof;
- a plurality of ultraviolet germicidal lamps intermediate said reflector and grid extending lengthwise of said housing and parallel to said grid;
- handle means on said housing to allow said portable lamp to be moved from a rest position and manually moved over a surface; and
- switching means to control operation of said ultraviolet lamps, said switching means including a normally closed switch manually depressible to an on position while said portable lamp is hand held.

* * * * *